United States Patent [19]

Horvitz et al.

[11] 4,322,355

[45] Mar. 30, 1982

[54] PRODUCTION OF 1,3-DIFUNCTIONAL COMPOUNDS

[75] Inventors: David Horvitz; William D. Baugh, both of Cincinnati, Ohio

[73] Assignee: National Distillers & Chemical Corp., New York, N.Y.

[21] Appl. No.: 140,511

[22] Filed: Apr. 15, 1980

[51] Int. Cl.³ .................... C07D 319/04; C07C 69/16; C07C 19/045
[52] U.S. Cl. ................................. 260/340.7; 560/238; 568/850; 568/852; 570/257; 570/261; 546/319
[58] Field of Search .................. 546/319; 560/238; 260/340.7; 568/841, 852, 850; 570/261, 257

[56] References Cited

U.S. PATENT DOCUMENTS 3,960,973 6/1976 Stapp .................................... 560/238
4,069,232 1/1978 Horvitz et al. .................... 260/343.6

OTHER PUBLICATIONS

Arundale et al., Chemical Reviews, vol. 51, Williams and Wilkins Pub. pp. 505-555, (1952)

*Primary Examiner*—Alan L. Rotman
*Attorney, Agent, or Firm*—Kenneth D. Tremain

[57] ABSTRACT

An improvement in the reaction of olefin with aldehyde, and optionally, carboxylic acid, in the liquid phase in the presence of a catalytically effective amount of strong acid to provide a 1,3-difunctional compound or a mixture of 1,3-difunctional compounds is provided by carrying out the aforesaid reaction in the further presence of a co-catalyst selected from the group consisting of antimony oxide, bismuth oxide, antimony salt, bismuth salt and mixtures thereof.

7 Claims, No Drawings

PRODUCTION OF 1,3-DIFUNCTIONAL COMPOUNDS

BACKGROUND OF THE INVENTION

1. Field of the Invention

This invention relates to processes for producing 1,3-difunctional compounds by the acid catalyzed reaction of an olefin with an aldehyde or aldehyde precursor.

2. Description of the Prior Art

Numerous modifications of the acid catalyzed reaction of olefin with aldehyde or aldehyde precursor (i.e., the Prins Reaction) to provide a variety of open chain and cyclic organic compounds are known.

In one category of reaction, olefin and aldehyde are co-reacted to largely produce formals, or cyclic diethers. U.S. Pat. No. 2,135,454 to McAlevy describes such a reaction, employing a catalyst system based upon a halogen acid and a boric acid, to provide formals. U.S. Pat. Nos. 2,158,031 and 2,289,548 to Lodger describe the reaction of formaldehyde and propylene to provide a substituted dioxane.

In accordance with U.S. Pat. No. 2,362,307 to Ritter, meta-dioxane is produced by reacting an aldehyde with an olefin in the presence of sulfuric acid. In the process of making meta-dioxanes disclosed in U.S. Pat. No. 2,368,494 to Rosen, tertiary unsaturated compounds are reacted with aldehydes in the presence of a dilute aqueous solution of boron trifluoride and optionally, a mineral acid such as sulfuric, hydrofluoric, hydrochloric or phosphoric acid. U.S. Pat. No. 2,423,783 to Lippincott relates to the preparation of 1,3-diols by the reaction of methyl alcohol with a 1,3-dioxane which has been obtained by the condensation of olefins and aldehydes. U.S. Pat. No. 2,426,017 to Hamblet, et al. and U.K. Specification No. 590,571 report that improved yields of 1,3-alkanediol cyclic formals can be obtained by including a small quantity of the formal along with the reactants propylene and formaldehyde. In addition, U.K. Specification No. 590,571 discloses formic acid as a catalyst for the reaction. U.S. Pat. No. 2,490,276 to Munday describes the reaction of 2,3-dimethyl butene-2 with formaldehyde in the presence of metallic chlorides such as stannic chloride, mercuric chloride and titanium chloride, or sulfuric or hydrochloric acid, to produce a cyclic diether. As disclosed in U.S. Pat. No. 2,504,732 to Rosen, aldehydes are condensed with olefins in the presence of aqueous boron fluorides to produce meta-dioxanes. In the process described in U.S. Pat. No. 2,997,480 to Hellin, isobutene is reacted with formaldehyde in the presence of a strong inorganic acid to provide 4,5-dimethylmetadioxane. According to U.S. Pat. No. 3,062,835 to Signorino, 2-methylbutene-2 is selectively reacted with formaldehyde in the presence of 2-methylbutene-1 and sulfuric acid to provide 4,4,5-trimethyl-meta-dioxane. U.S. Pat. No. 3,154,563 and French Pat. No. 1,292,840 each describe the use of an acidic cation-exchange resin catalyst in the reaction of isobutene and formaldehyde to provide 4,4-dimethyldioxane. Following the process described in U.S. Pat. No. 3,414,588 to Jones, aldehydes and olefins are co-reacted in the presence of a base exchanged alumino-silicate catalyst to provide alkyl-meta-dioxane. U.S. Pat. No. 3,438,977 to Fetterly, et al. describes the production of meta-dioxanes or acetate esters by the reaction of olefin and aldehyde in a diluent such as acetic acid, propionic acid or butyric acid, in the presence of cationic exchange resins which contain sulfonic, phosphonic, phosphonous, arsenic and like acid groups. From U.S. Pat. No. 3,818,043 to Starks, it is known to prepare a mixture containing unsaturated 1-alcohols, diols and dioxanes by the reaction of olefin and aldehyde in the presence of an aqueous solution of a strong acid such as sulfuric acid and cuprous chloride. U.S. Pat. No. 4,017,518 to Gorbunov, et al. describes the preparation of 4,4-dimethyldioxane-1,3 by reacting isobutylene with formaldehyde in the presence of an inorganic salt of a mineral acid. U.S. Pat. No. 4,069,232 to Horvitz, et al. discloses the preparation of, among others, meta-dioxanes, by the protic acid catalyzed reaction of an olefin with an aldehyde. 1,3-Dioxane can be produced, along with various esters and other compounds, when acetic acid is present in the reaction media.

In another category of reaction, olefin and aldehyde are co-reacted primarily to provide glycol monoesters and diesters. Illustrative of such a reaction are U.S. Pat. Nos. 3,438,997 to Fetterly, et al. and 4,069,232 to Horvitz, et al., and French Pat. Nos. 717,712 and 933,182, each of which describes the reaction of aldehyde and olefin in the presence of a carboxylic acid and a strong mineral acid to provide glycol esters. U.S. Pat. No. 3,438,997 to Fetterly, et al. specifically relates to the preparation of metadioxanes or acetate esters by the reaction of olefin and aldehyde in a lower alkyl monocarboxylic acid, e.g., acetic acid, propionic acid or butyric acid, in the presence of acidic cationic exchange resins. U.S. Pat. No. 4,069,232 to Horvitz, et al. discloses the preparation, inter alia, of glycol monoesters and diesters by the reaction of olefin with an aldehyde in the presence of a carboxylic acid employing a protic acid such as hydriodic acid or hydrobromic acid. French Pat. Nos. 717,712 and 933,182 each disclose the preparation of glycol esters by the reaction of an olefin with an aldehyde in the presence of acetic acid and sulfuric acid as catalyst.

Another category of the Prins Reaction yields glycols for the most part. According to U.S. Pat. No. 2,143,370 to Fitzky, butylene glycol is obtained by reacting propylene with formaldehyde in the presence of a hydrogen halide and optionally, a heavy metal halide such as zinc chloride, calcium chloride, magnesium chloride or mercury chloride. In U.S. Pat. No. 2,368,494 to Rosen, 1,3-butylene glycols are obtained by reacting tertiary unsaturated compounds with aldehydes in the presence of a dilute aqueous solution of boron trifluoride and optionally, a mineral acid. Glycols are prepared in accordance with the process of U.S. Pat. No. 2,449,001 to Mikeska, et al. by reacting an olefin with an aldehyde in the presence of a dilute ternary or quaternary mineral acid such as sulfuric, sulfurous, phosphoric, phosphorous, fluosulfonic, fluosilicic, dihydroxy fluoboric, and hydrofluoboric acids or acid-acting metallic salts of polybasic mineral acids such as $NaHSO_4$, $NaH_2PO_4$, $ZnSO_4$, $Fe_2(SO_4)_3$ or $Al_2(SO_4)_3$. The process for preparing glycols disclosed in U.S. Pat. No. 3,414,588 to Jones calls for reacting aldehydes and olefins in the presence of a base exchanged aluminosilicate catalyst. The process of U.S. Pat. No. 3,818,043 to Starks referred to above provides a mixture of 1-alcohols, diols and dioxanes. U.S. Pat. No. 4,069,232 to Horvitz, et al. describes the protic acid catalyzed reaction of olefin and aldehyde to provide 1,3-glycols and a variety of other 1,3-difunctional compounds. Related processes for obtaining 1,3-difunctional compounds are described elsewhere. For example, see Arundale & Mikeska, *Chem. Revs.* 51, 505–55 (1952); Roberts, *Friedel Craft and Related Reactions*, Olah ed., Volume II, pages 1175–1210, Inter Science Publishers, New York, 1964; Walker, *Formaldehyde*, 3rd Ed. Reinhold Publishing Corp., New York, 1964, pages 416–28; and U.S. Pat. No. 3,586,698 to Ishii, et al.

Finally, the reaction of olefin and aldehyde can be made to provide halogenated alcohols and esters as described in U.S. Pat. No. 4,069,232 to Horvitz, et al. in which a mixture of 3-hydroxypropyliodide and its corresponding acetic acid ester 3-iodopropylacetate is obtained by reacting ethylene with formaldehyde in the presence of acetic acid and hydriodic acid.

SUMMARY OF THE INVENTION

In accordance with the invention herein, the reaction of olefin with aldehyde or aldehyde precursor in the liquid phase in the presence of a catalytically effective amount of strong acid, and optionally, a carboxylic acid, to provide one or a mixture of 1,3-difunctional compounds provides unexpectedly higher yields when carried out in the further presence of a co-catalyst selected from the group consisting of antimony oxide, antimony salt, bismuth oxide and bismuth salt.

The products of the foregoing reaction between olefin and aldehyde are 1,3-difunctional compounds of the formula

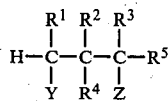

in which $R^1$, $R^2$, $R^3$, $R^4$ and $R^5$ are from the group consisting of hydrogen, alkyl, aryl, cycloalkyl, aralkyl, alkaryl or heterocylic groups of 1–18 carbon atoms, Y and Z are each hydroxyl, $R^6COO$—, Cl, Br, I or E, or together are —$OCH(R^1)O$—, E is an oxygen-bonded inorganic ester moiety such as nitrate, sulfate, phosphate, borate, arsenate and the like, and $R^6$ is hydrogen, alkyl or 1–18 carbon atoms, aryl of 6–18 carbon atoms, alkaryl of 6–18 carbon atoms or aralkyl of 6–18 carbon atoms. $R^2$ and $R^3$ together may comprise a trimethylene or tetramethylene group to form a 5- or 6-membered alicyclic structure with the two carbon atoms on which they are substituted. The group $R^1$ is the group which is part of the aldehyde, $R^1CHO$, which is reacted with an olefin to produce the desired 1,3-difunctional compound. When diolefins are employed, corresponding 1,3-difunctional groups may be produced at each double bond.

Examples of 1,3-difunctional compounds produced in the first step of the instant invention include 1,3-dioxane, 1,3-diacetoxypropane, 3-hydroxypropyl acetate, 3-hydroxypropyl iodide, 3-iodopropyl acetate, 1,3-diiodopropane, 1,3-propanediol, 4,4-dimethyl-1,3-dioxane, 5,5-dimethyl-1,3-dioxane, 3-hydroxypropyl bromide, 3-bromopropyl acetate, 1,3-dibromopropane, and the like.

In addition to the 1,3-difunctional compounds produced, other by-products, and in particular, 1,2-difunctional and monofunctional compounds such as 1-iodo-2-acetoxyethane, 1-chloro-2-acetoxyethane, 1,2-diacetoxyethane, 1,2-diiodoethane, 1,2-dichloroethane, ethyl iodide, ethyl chloride, ethyl acetate, and the like, may be formed by the addition of acid to olefin in the process described herein. These by-products, which are useful in themselves or as intermediates, can be readily separated from the 1,3-difunctional compounds employing routine procedures such as fractional distillation.

The quantitative distribution of the 1,3-difunctional compounds and any other compounds present in the product mixture obtained in accordance with the process of this invention will depend in part upon the specific reaction conditions selected. The mixture can be resolved into its individual components employing known and conventional techniques, e.g., fractional distillation, or the mixture can be directly used as the starting material for the manufacture of gammabutyrolactone as described in U.S. Pat. No. 4,069,232 to Horvitz, et al.

The term "strong acid" as used herein shall be understood to refer to any mineral or organic acid, a one molar aqueous solution of which possesses a pH of not more than about 2.

DESCRIPTION OF THE PREFERRED EMBODIMENTS

The olefins which can be used in the preparation of the 1,3-difunctional compounds according to the process of this invention include any of the mono- or diolefins containing 2–18 carbon atoms. The olefins can be substituted with aromatic, alicyclic or heterocyclic groups and the unsaturation can exist at any part of the olefinic carbon atom chain and also in cyclic moieties. Both conjugated and monconjugated diolefins can be employed. Thus, among the olefins which can be used in this invention are ethylene, propylene, butene-1, cis- and transbutene-2, isobutylene, hexene-2, diisobutylene, trimethylethylene, 1,5-hexadiene, cyclohexene, cyclopentadiene, butadiene, isoprene, 1,4-pentadiene, 1,3-hexadiene, cyclooctadiene, 1-sec-butyl-2-methylstyrene, propenylbenzene, beta-vinylnaphthalene, beta-vinylpyridine, and the like.

The aldehydes which can be selected for reaction with olefin can contain 1–18 carbon atoms, one or two aldehyde groups and can also contain aromatic, alicyclic or heterocyclic groups. Additionally, the aldehyde reactant can also be in any form which readily generates the aldehyde such as in the form of an acetal or semi-acetal, a bisulfite addition product, a bis-methylene ester, or a cyclic or linear oligomer. Examples of aldehydes or aldehyde-generating compounds which can be employed include formaldehyde, paraformaldehyde, trioxane, methylal, hexamethylene tetramine, formaldoxime, sodium formaldehydesulfoxylate, acetaldehyde, propionaldehyde, n-butyraldehyde, benzaldehyde, cyclopentane carboxaldehyde, terephthaldehyde, beta-pyridinecarboxaldehyde, alpha-naphthaldehyde, beta-pyridinecarboxaldehyde, alpha-naphthaldehyde, and the like.

The general conditions for effecting the reaction of the olefins and aldehydes to produce 1,3-difunctional compounds are known and reference may be made to the literature in this regard (cf. Arundale & Mikeska, *Chem. Revs.* 51, 505–55 (1952); Roberts, *Friedel Crafts and Related Reactions*, Olah ed., Volume II, pages 1175–1210, Inter Science Publishers, New York, 1964; Walker, *Formaldehyde*, 3rd Ed. Reinhold Publishing Corp., New York, 1964, pages 416–28; U.S. Pat. No. 3,586,698 to Ishii, et al.; and U.S. Pat. No. 4,069,232 to Horvitz, et al., the disclosures of which are incorporated herein by reference). The method and conditions employed depend greatly on the particular olefin and aldehyde used and the type of product desired.

It is possible to obtain meta-dioxanes, glycols, or esters depending on the conditions which are used. Acid concentration, temperature and duration of the reaction vary with the product desired and the nature of the olefin. In the presence of carboxylic acid, the corresponding esters are obtained. Illustrative of carboxylic acids which can optionally be included in the reaction media herein are the aliphatic monocarboxylic acids including formic, acetic, propionic, butyric, isobutyric, valeric, isovaleric, caproic, enanthic, caprylic, pelargonic, capric, lauric, myristic, palmitic, stearic, hexacosanoic, and tricosanoic acid. Aliphatic carboxylic acids having two or more —COOH groups are also useful, e.g., oxalic, malonic, succinic, glutaric and adipic acid. The process of this invention also finds useful alicyclic, aromatic and heterocylic carboxylic acids having one or more —COOH groups such as cyclopropanecarboxylic, cyclopentanecarboxylic, hexahydrobenzoic, benzoic, 1-naphthoic, 2-naphthoic, orthotoluic, meta-toluic, paratoluic, ortho-chlorobenzoic, meta-chlorobenzoic, parachlorobenzoic, orthonitrobenzoic, meta-nitrobenzoic, parahydroxybenzoic, anthranilic, meta-aminobenzoic, para-aminobenzoic, phenylacetic, 2,4-dichlorophenyloxyacetic, hydrocinnamic, 2-phenylbutyric, 1-naphthaleneacetic, phthalic, picolinic, nicotinic, 3-indoleacetic, thiophenecarboxylic, quinolinic, and 2-methyl-3-indoleacetic acid. Of the aforesaid carboxylic acids, the lower aliphatic monocarboxylic acids are preferred and of these, formic and acetic acid are most preferred.

The concentration of aldehyde can vary from 0.1 M to 15 M with a preferred range of 0.2 M to 5 M. The olefin can serve as a solvent, or other organic solvents, and reaction inert liquids can be used, e.g., aliphatic or aromatic hydrocarbons such as hexane, cyclohexane, benzene, chlorobenzene or dichloroethane. Amounts of water of up to 50 weight percent of the entire reaction medium, can also serve as a diluent and/or reactant. The olefin should be present in a mole ratio relative to the aldehyde of at least 0.5:1 but can be present in any excess greater than that ratio. In general, a ratio of olefin to aldehyde of 1:1 to 2:1 is preferred. However, when a gaseous or highly volatile olefin is used, such as ethylene or propylene, elevated pressures are desirable to obtain sufficient solubility, and in such cases, the ratio of olefins to aldehydes may be in considerable excess over the 2:1 ratio. The temperature to be used in the reaction depends greatly on the olefin employed and can vary from ambient temperature to 250° C. The preferred temperature in the case of ethylene is 120°–200° C. Pressure, of course, must be maintained at a level which will maintain the reaction medium in the liquid state. The preferred duration of reaction is also strongly dependent on the olefin and aldehyde used and on the acid concentration. The time required can vary from 15 minutes to 10 hours.

Strong acids which can be employed herein with good results include the halogen acids such as hydrofluoric, hydrochloric, hydrobromic and hydriodic acid, nitric acid, sulfuric acid, organic acids such as toluenesulfonic acid, trifluoroacetic acid, and the like. Hydriodic acid is especially preferred. The amount of strong acid employed can vary over wide limits provided, of course, the acid is present in at least a catalytically effective amount. In general, from about 0.1 to about 20 parts by weight or even higher, and preferably from about 1.0 to about 10 parts by weight, of strong (concentrated) acid based on the total weight of the reactants are effective.

The co-catalysts which are essential to the improved results obtained in accordance with the present invention can be selected from among any of the oxides and salts of antimony and bismuth. The simple and complex oxides, and the halide salts, of antimony and bismuth are particularly advantageous. Thus, for example, antimony oxide, bismuth oxide, mixed oxides of antimony and bismuth, and the fluorides, chlorides, bromides and iodides of antimony and bismuth are especially preferred for use herein. The oxides, if used, can exist in any of their oxidation states. The amounts of co-catalyst employed can be widely varied, with molar ratios of strong acid to co-catalyst of from about 0.5:1 to 20:1, and preferably from 1:1 to 10:1, being entirely effective. While it is not necessary to provide the co-catalysts of this invention with a support, it is generally advantageous to deposit the catalysts upon a carrier such as any of the known and conventional catalyst carrier materials since catalytic efficiency will thereby be significantly improved. Thus, the co-catalysts herein can advantageously be supported upon silica, alumina, zirconia, silica alumina, silicon carbide, alundum and inorganic silicate in an amount of from about 10 percent to about 90 percent catalyst by weight of support material. Preparation of the supported catalysts follows well-established procedures. The finely divided support material is impregnated with an aqueous solution of water soluble compounds of antimony and/or bismuth, followed by drying and calcining from about 600° C. in the presence of oxygen to about 1100° C. (but not exceeding the sintering temperature of the support) for from about 1 to about 48 hours to provide the corresponding metal oxides. Examples of suitable water soluble metal compounds which can be used in the preparation of the supported catalysts include antimony fluoride and bismuth tartrate.

The following examples further illustrate the invention. Analysis of the mixture of reaction products was by the following conditions: 4½′×⅛″ Porapak Q column, 230° C.

EXAMPLES 1 to 19

| Example | 36.3 wt % aq. HCHO (ml) | Glacial Acetic Acid (ml) | 57 wt % aq. HI (ml) | Co-catalyst (gm) | Ethylene (psi) | Temp (°C.) | Time (hr) | VPC Analysis Peaks | Retention Time (min) | Chart Divisions | Difunctional Compounds |
|---|---|---|---|---|---|---|---|---|---|---|---|
| 1 | 1.5 | 6.5 | 2.0 | — | 1000 | 145 | 8 | A | 5.6 | 53 | 1-iodo-2-acetoxyethane |
|   |     |     |     |   |      |     |   | B | 10.0 | 60 | 1,3-diacetoxypropane |
|   |     |     |     |   |      |     |   | C | 11.5 | 46.5 | 1-iodo-3-acetoxypropane |
| 2 | 1.5 | 6.5 | 2.0 | $Bi_2O_3$ (0.5) | 1000 | 145 | 8 | A | 5.5 | 85.5 | 1-iodo-2-acetoxyethane |
|   |     |     |     |   |      |     |   | B | 9.4 | 121.0 | 1,3-diacetoxypropane |
|   |     |     |     |   |      |     |   | C | 11.0 | 61.2 | 1-iodo-3-acetoxypropane |
| 3 | 1.5 | 6.5 | 2.0 | $Bi_2O_3$ | 1000 | 145 | 8 | A | 5.5 | 66.0 | 1-iodo-2-acetoxyethane |

EXAMPLES 1 to 19

| Example | 36.3 wt % aq. HCHO (ml) | Glacial Acetic Acid (ml) | 57 wt % aq. HI (ml) | Co-catalyst (gm) | Ethylene (psi) | Temp (°C.) | Time (hr) | Peaks | Retention Time (min) | Chart Divisions | Difunctional Compounds |
|---|---|---|---|---|---|---|---|---|---|---|---|
| | | | | (0.25) | | | | B | 9.5 | 106.0 | 1,3-diacetoxypropane |
| | | | | | | | | C | 11.0 | 63.0 | 1-iodo-3-acetoxypropane |
| 4 | 1.5 | 6.5 | 2.0 | — | 1000 | 145 | 8 | A | 5.8 | 46.2 | 1-iodo-2-acetoxyethane |
| | | | | | | | | B | 10.4 | 49 | 1,3-diacetoxypropane |
| | | | | | | | | C | 11.7 | 32 | 1-iodo-3-acetoxypropane |
| 5 | 1.5 | 6.5 | 2.0 | Bi₂O₃ (0.75) | 1000 | 145 | 8 | A | 5.7 | 73.5 | 1-iodo-2-acetoxyethane |
| | | | | | | | | B | 9.8 | 95.7 | 1,3-diacetoxypropane |
| | | | | | | | | C | 11.2 | 49.5 | 1-iodo-3-acetoxypropane |
| 6 | 1.5 | 6.5 | 2.0 | Bi₂O₃ (1.0) | 1000 | 145 | 8 | A | 5.6 | 67.5 | 1-iodo-2-acetoxyethane |
| | | | | | | | | B | 10.0 | 68.5 | 1,3-diacetoxypropane |
| | | | | | | | | C | 11.4 | 38.0 | 1-iodo-3-acetoxypropane |
| 7 | 1.5 | 6.5 | 2.0 | Bi₂O₃ (1.0) | 1000 | 145 | 8 | A | 5.6 | 59.0 | 1-iodo-2-acetoxyethane |
| | | | | | | | | B | 9.8 | 99.0 | 1,3-diacetoxypropane |
| | | | | | | | | C | 11.3 | 59.0 | 1-iodo-3-diacetoxypropane |
| 8 | 1.5 | 7.35 | 1.15 | — | 1000 | 145 | 8 | A | 5.3 | 41.0 | 1-iodo-2-acetoxyethane |
| | | | | | | | | B | 10.1 | 26.1 | 1,3-diacetoxypropane |
| 9 | 1.5 | 7.35 | 1.15 | BiI₃ (1.26) | 1000 | 145 | 8 | A | 5.1 | 69.0 | 1-iodo-2-acetoxyethane |
| | | | | | | | | B | 9.0 | 121.0 | 1,3-diacetoxypropane |
| 10 | 1.5 | 7.78 | .72 | BiI₃ (1.90) | 1000 | 145 | 8 | A | 5.2 | 50.8 | 1-iodo-2-acetoxyethane |
| | | | | | | | | B | 9.9 | 30.3 | 1,3-diacetoxypropane |
| 11 | 1.5 | 6.5 | 2.0 | — | 1000 | 145 | 8 | A | 5.4 | 35 | 1-iodo-2-acetoxyethane |
| | | | | | | | | B | 10.0 | 40 | 1,3-diacetoxypropane |
| 12 | 1.5 | 6.5 | 2.0 | Sb₂O₃ (0.25) | 1000 | 145 | 8 | A | 5.4 | 51 | 1-iodo-2-acetoxyethane |
| | | | | | | | | B | 9.7 | 70 | 1,3-diacetoxypropane |
| | | | | | | | | C | 11.0 | (masked) | 1-iodo-3-acetoxypropane |
| 13 | 1.5 | 6.5 | 2.0 | Sb₂O₃ (0.50) | 1000 | 145 | 8 | A | 5.4 | 54 | 1-iodo-2-acetoxyethane |
| | | | | | | | | B | 9.7 | 73.8 | 1,3-diacetoxypropane |
| | | | | | | | | C | 11.0 | (masked) | 1-iodo-3-acetoxypropane |
| 14 | 1.5 | 6.5 | 2.0 | — | 1000 | 145 | 8 | A | 5.3 | 35.5 | 1-iodo-2-acetoxyethane |
| | | | | | | | | B | 9.8 | 40.5 | 1,3-diacetoxypropane |
| | | | | | | | | C | 11.0 | (masked) | 1-iodo-3-acetoxypropane |
| 15 | 1.5 | 6.5 | 2.0 | Sb₂O₃ (0.75) | 1000 | 145 | 8 | A | 5.3 | 46.5 | 1-iodo-2-acetoxyethane |
| | | | | | | | | B | 10.0 | 30.0 | 1,3-diacetoxypropane |
| | | | | | | | | C | 11.0 | (masked) | 1-iodo-3-acetoxypropane |
| 16 | 1.5 | 6.5 | 2.0 | Sb₂O₃ (1.0) | 1000 | 145 | 8 | A | 5.3 | 49.5 | 1-iodo-2-acetoxyethane |
| | | | | | | | | B | 10.0 | 30.8 | 1,3-diacetoxypropane |
| | | | | | | | | C | 11.0 | (masked) | 1-iodo-3-acetoxypropane |
| 17 | 1.5 | 7.20 | 1.31 | — | 1000 | 145 | 8 | A | 5.5 | 28.3 | 1-iodo-2-acetoxyethane |
| | | | | | | | | B | 10.7 | 19 | 1,3-diacetoxypropane |
| 18 | 1.5 | 7.20 | 1.31 | SbI₃ (0.86) | 1000 | 145 | 8 | A | 5.3 | 46.5 | 1-iodo-2-acetoxyethane |
| | | | | | | | | B | 9.6 | 76.5 | 1,3-diacetoxypropane |
| 19 | 1.5 | 8.5 | — | SbI₃ (2.60) | 1000 | 145 | 8 | A | 5.5 | 27.8 | 1-iodo-2-acetoxyethane |
| | | | | | | | | B | 10.8 | 14.4 | 1,3-diacetoxypropane |

As the data set forth in Examples 1 to 19 demonstrate, the use of an oxide or salt of antimony and/or bismuth as a co-catalyst in the reaction of olefin and aldehyde provides significantly increased yields of 1,3-difunctional compounds compared to the same reaction catalyzed with strong acid alone. dehyde. Ethylene was charged at 1000 psi and reaction temperature and time were 145° C. and 8 hours, respectively. These data further demonstrate the advantage of employing an antimony and/or bismuth oxide or salt as co-catalyst. It is noted that the co-catalysts alone are not effective catalysts for the reaction.

EXAMPLES 20 to 28

| Example | 36.3 wt % aq. HCHO (ml) | Glacial Acetic Acid (ml) | 57 wt % aq. HI (ml) | Water (ml) | 95 wt % aq. Paraformaldehyde (ml) | Co-catalyst (gm) | Yield (%) |
|---|---|---|---|---|---|---|---|
| 20 | 1.5 | 6.5 | 2.0 | — | — | — | 14.46 |
| 21 | 1.5 | 7.35 | 1.15 | — | — | BiI₃ (1.26) | 41.77 |
| 22 | — | 7.35 | 1.15 | 1.5 | 0.5 | BiI₃ (1.26) | 39.52 |
| 23 | — | 8.0 | 2.0 | — | 0.5 | — | 26.66 |
| 24 | — | 8.70 | 1.30 | — | 0.5 | SbI₃ (0.86) | 57.71 |
| 25 | 1.5 | 7.20 | 1.30 | — | — | SbI₃ (0.86) | 36.51 |
| 26 | 1.5 | 6.5 | 2.0 | — | — | — | 18.26 |
| 27 | 1.5 | 8.5 | — | — | — | — | 0 |
| 28 | 1.5 | 8.5 | — | — | — | BiI₃ (2.97) | 0 |

All yields in Examples 20 to 28 are reported as moles of 1,3-diacetoxypropane produced per mole of formal-

EXAMPLES 29 to 56

By way of further comparison, Examples 29 to 34 were carried out employing hydriodic acid as the sole catalyst agent. The yields of 1,3-difunctional compounds are given in Table I and average 31.4%. Examples 35 to 56 illustrate essentially the same reaction but with varying amounts of bismuth oxide co-catalyst in accordance with this invention. The yields of 1,3-difunctional compounds are given in Table II and average 40.7%, a substantially higher average yield than that obtained in the absence of co-catalyst.

TABLE I

| Example | HCHO (from paraformaldehyde) (mmoles) | HI (milliequiv.) | Ratio HI/HCHO | Conc. HI/HCHO moles/liter | Yield (%) of 1,3-Difunctional Compounds |
|---|---|---|---|---|---|
| 29 | 7.91 | 15.1 | 1.8 | 1.15 | 28.8 |
| 30 | 7.91 | 22.7 | 2.7 | 1.53 | 36.9 |
| 31 | 7.91 | 30.3 | 3.6 | 1.91 | 28.8 |
| 32 | 15.9 | 22.7 | 1.4 | 1.93 | 37.8 |
| 33 | 31.6 | 22.7 | 0.68 | 2.71 | 24.6 |
| 34 | 31.6 | 30.3 | 0.91 | 3.09 | 31.5 |

In the above examples, the charges included 16 to 18 ml. glacial acetic acid. Ethylene pressure was 1000 psi and the reaction temperature and time were 145° C. and 8 hours, respectively.

TABLE II

| Example | HI milliequiv. | HI Normality | $Bi_2O_3$ milliequiv. | Reaction Temp. °C. | Reaction Time Hrs. | Yield (%) of 1,3-Difunctional Compounds |
|---|---|---|---|---|---|---|
| 35 | 22.7 | 1.14 | 3.22 | 144 | 8 | 44.0 |
| 36 | 22.7 | 1.14 | 3.22 | 160 | 7 | 40.8 |
| 37 | 22.7 | 1.14 | 3.22 | 200 | 3 | 35.2 |
| 38 | 22.7 | 1.14 | 3.22 | 200 | 6 | 37.9 |
| 39 | 30.3 | 1.51 | 6.44 | 135 | 8 | 36.7 |
| 40 | 27.7 | 1.14 | 6.44 | 145 | 8 | 37.2 |
| 41 | 27.7 | 1.14 | 6.44 | 145 | 8 | 26.5 |
| 42 | 30.3 | 1.51 | 6.44 | 145 | 8 | 35.8 |
| 43 | 30.3 | 1.51 | 6.44 | 145 | 8 | 27.0 |
| 44 | 37.9 | 1.90 | 6.44 | 145 | 8 | 27.0 |
| 45 | 22.7 | 1.14 | 6.44 | 160 | 7 | 39.3 |
| 46 | 22.7 | 1.14 | 6.44 | 200 | 3 | 37.8 |
| 47 | 22.7 | 1.14 | 6.44 | 200 | 6 | 37.3 |
| 48 | 30.3 | 1.51 | 12.87 | 135 | 8 | 40.8 |
| 49 | 22.7 | 1.14 | 12.87 | 145 | 8 | 25.3 |
| 50 | 22.7 | 1.14 | 12.87 | 160 | 7 | 41.1 |
| 51 | 22.7 | 1.14 | 12.87 | 200 | 6 | 34.8 |
| 52 | 22.7 | 1.14 | 12.87 | 200 | 3 | 38.3 |
| 53 | 30.3 | 1.51 | 12.87 | 145 | 8 | 51.3 |
| 54 | 30.3 | 1.51 | 19.31 | 145 | 8 | 49.7 |
| 55 | 37.9 | 1.90 | 19.31 | 145 | 8 | 33.9 |
| 56 | 30.3 | 1.51 | 12.87 | 145 | 8 | 42.7 |

In the above examples, the charges included 31.6 milliequivalents of paraformaldehyde and 15, 16 or 17 ml. glacial acetic acid corresponding to 22.7, 30.3 or 37 milliequivalents of HI. Ethylene pressure was 1000 psi.

What is claimed is:

1. In a process for preparing a compound or a mixture of compounds selected from the group consisting of 1,3-dioxane, 1,3-diacetoxypropane, 3-hydroxypropyl acetate, 3-hydroxypropyl iodide, 3-iodopropyl acetate, 1,3-diiodopropane, 1,3-propanediol, 4,4-dimethyl-1,3-dioxane, 5,5-dimethyl-1,3-dioxane, 3-hydroxypropyl bromide, 3-bromopropyl acetate, 1,3-dibromopropane, 1-iodo-2-acetoxyethane or 1-iodo-3-acetoxypropane, by the reaction of an olefin with an aldehyde and/or a compound which, under the reaction conditions, provides an aldehyde, in the liquid phase in the presence of a strong acid catalyst, the improvement which comprises carrying out said reaction in the presence of a co-catalyst selected from the group consisting of bismuth oxide, antimony oxide, mixed oxides of antimony and bismuth, and the fluorides, chlorides, bromides, and iodides of antimony and bismuth.

2. The process of claim 1 wherein a carboxylic acid is present with the olefin and aldehyde.

3. The process of claim 2 wherein the carboxylic acid is formic, acetic, propionic, butyric, isobutyric, valeric, isovaleric, caproic, enanthic, caprylic, pelargonic, capric, lauric, myristic, palmitic, stearic, hexacosanoic, tricosanoic, oxalic, malonic, succinic, glutaric, adipic, cyclopropanecarboxylic, cyclopentanecarboxylic, hexahydrobenzoic, benzoic, 1-naphthoic, 2-naphthoic, ortho-toluic, meta-toluic, para-toluic, ortho-chlorobenzoic, meta-chlorobenzoic, para-chlorobenzoic, ortho-nitrobenzoic, meta-nitrobenzoic, para-hydroxybenzoic, anthranilic, meta-aminobenzoic, paraminobenzoic, phenylacetic, 2,4-dichlorophenyloxyacetic, hydrocinnamic, 2-phenylbutyric, 1-naphthaleneacetic, phthalic, picolinic, nicotinic, 3-indoleacetic, thiophenecarboxylic, quinolinic, 2-methyl-3-indoleacetic, or mixtures of any of the foregoing.

4. The process of claim 2 wherein water is present with the olefin, aldehyde and carboxylic acid.

5. The process of claim 1 wherein the strong acid is hydrofluoric, hydrochloric, hydrobromic, hydriodic, nitric, sulfuric, toluenesulfonic or trifluoroacetic acid, or mixtures of any of the foregoing.

6. The process of claim 1 wherein the catalyst is an oxide of antimony or bismuth, or a mixed oxide of antimony or bismuth, supported upon a carrier.

7. The process of claim 6 wherein the carrier is silica, alumina, zirconia, silica alumina, silicon carbide, alundum or inorganic silicate.

* * * * *